United States Patent
Paige et al.

(10) Patent No.: US 7,024,935 B2
(45) Date of Patent: Apr. 11, 2006

(54) ELECTROMAGNETIC ACOUSTIC TRANSDUCERS

(75) Inventors: David Paige, Newcastle upon Tyne (GB); Robert Andrew Mercel, Ashington (GB)

(73) Assignee: Pii Limited, Cramlington (GB)

( * ) Notice: Subject to any disclaimer, the term of this patent is extended or adjusted under 35 U.S.C. 154(b) by 43 days.

(21) Appl. No.: 10/502,731

(22) PCT Filed: Jan. 28, 2003

(86) PCT No.: PCT/GB03/00378

§ 371 (c)(1),
(2), (4) Date: Mar. 29, 2005

(87) PCT Pub. No.: WO03/067247

PCT Pub. Date: Aug. 14, 2003

(65) Prior Publication Data

US 2005/0172719 A1 Aug. 11, 2005

(30) Foreign Application Priority Data

Feb. 5, 2002 (GB) .................................. 0202658

(51) Int. Cl.
*G01N 29/06* (2006.01)
*G01N 29/24* (2006.01)

(52) U.S. Cl. ...................................................... 73/643
(58) Field of Classification Search ................. 73/643, 73/629, 620
See application file for complete search history.

(56) References Cited

U.S. PATENT DOCUMENTS

| 3,898,555 | A | * | 8/1975 | Tellerman | ............... 324/207.13 |
| 4,678,993 | A | * | 7/1987 | Vinnemann et al. | ... 324/207.13 |
| 4,727,321 | A | * | 2/1988 | Huschelrath | ................. 324/226 |
| 5,121,058 | A | * | 6/1992 | Allison et al. | ............... 324/235 |
| 5,987,993 | A | * | 11/1999 | Meier et al. | ................... 73/643 |
| 6,009,756 | A | * | 1/2000 | Willems et al. | ................ 73/643 |
| 6,766,694 | B1 | * | 7/2004 | Hubschen | ..................... 73/643 |

FOREIGN PATENT DOCUMENTS

WO    WO 200204135 A1 * 1/2002

* cited by examiner

*Primary Examiner*—Hezron Williams
*Assistant Examiner*—Rose M. Miller
(74) *Attorney, Agent, or Firm*—Stites & Harbison PLLC; Ross F. Hunt, Jr.

(57) ABSTRACT

An electromagnetic acoustic transducer for exciting ultrasound in a ferromagnetic material under test (2), includes a magnetic unit (6) arranged to be moved relative to the material under test (2) to magnetize a surface layer of the material, and an electrical winding (8) supplied by an alternating current source, the magnetic unit (6) and the electric winding (8), in use, being applied in sequence to the material under test (2) whereby the electrical winding (8) is positioned adjacent the material subsequent to magnetization thereof by the magnetic unit (8), the alternating magnetic flux created by the winding (8) interacting with the remanent magnetization of the material to create ultrasonic vibration of the material.

9 Claims, 3 Drawing Sheets

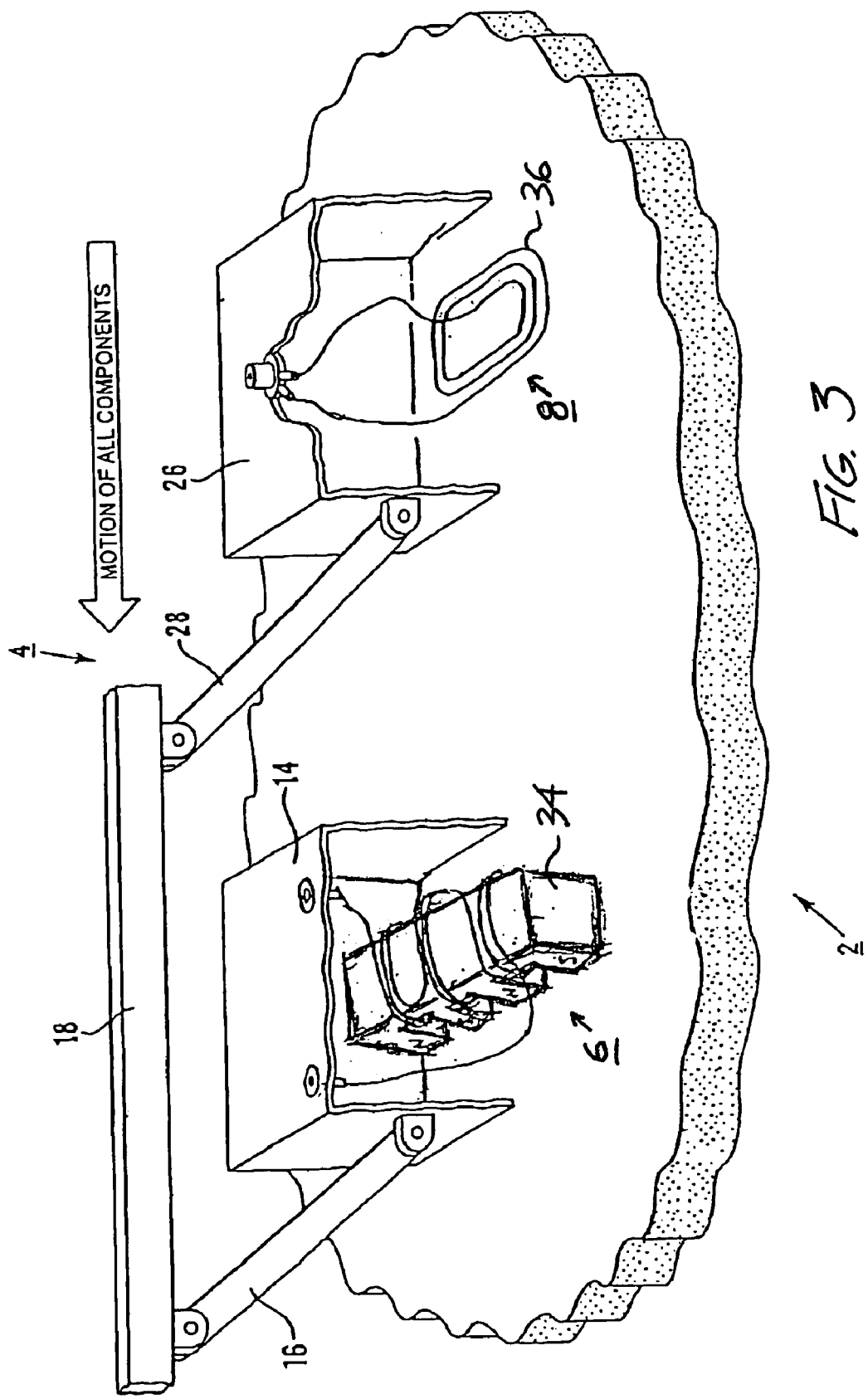

ELECTROMAGNETIC ACOUSTIC TRANSDUCERS

TECHNICAL FIELD

This invention relates to electromagnetic acoustic transducers for inspecting ferromagnetic materials, particularly though not exclusively gas pipelines.

BACKGROUND ART

Non-destructive inspection of metallic materials, for example materials from which structural engineering components are composed, can be undertaken by introducing ultrasound into the material. Information about defects within the material can then be obtained by receiving and analysing the ultrasound signal after it has travelled within the material.

Ultrasound is commonly introduced into a material by means of piezoelectric transducers, which have a face that vibrates mechanically at ultrasound frequencies. The ultrasound is normally passed into the material to be tested by a coupling medium, for example water, which is introduced between the transducer face and the material under test.

For the ultrasonic testing of some materials, it is impractical, or in some cases disadvantageous, to introduce a coupling medium, for example during the inspection of gas pipelines by a moving inspection vehicle, commonly referred to as an inspection pig. Under these circumstances a means of dry-coupling the ultrasound into the material is required.

Ultrasound can be excited in electrically conductive materials by the application of a high frequency magnetic field in the presence of a second magnetic field which is permanent or varies very slowly. Devices for achieving this are called electromagnetic acoustic transducers (hereinafter referred to as EMATs).

For EMATs used in conjunction with a permanent magnetic field, the usual means of operation is that the high frequency magnetic field created by the EMAT produces electrical eddy currents within the material. These eddy currents flow in the presence of the permanent magnetic field and generate lorentz forces acting within the material. These forces create mechanical displacements within the material, which propagate as acoustic waves. In the ferromagnetic material there are two other mechanisms by which the high frequency magnetic field initiates acoustic waves, namely magnetostriction and magnetic body forces. These additional forces can also play a part in the initiation of acoustic waves.

Numerous designs for EMATs have been proposed each of which is characterised by a particular geometry for the two key components of the EMAT, namely the mechanism for generating a permanent magnetic field in the test specimen and the electrical winding used to carry the high frequency electrical current. The result of altering these components of the EMAT can be that the ultrasound introduced into the test specimen is altered in the direction it is radiated or in the propagation mode, for example compression mode or transverse (shear) mode.

Nearly all EMAT transducers suffer from 'barkhausen' noise when moved over the surface of a ferromagnetic system. Barkhausen noise is due to the discontinuous motion of ferromagnetic domain boundaries during changes in the bulk magnetisation of ferromagnetic material below the saturating field for the material. It is a consequence of the magnetising components within the EMAT transducer. Barkhausen noise can be a severe problem for EMAT pipe inspection using pigs, because the inspection is carried out at speed.

There are a variety of compromises made in the design of any EMAT, but the arrangement of the magnetic field components and the electrical windings can only be manipulated within limits set by the fundamental physical method of their operation. Each type of EMAT has its fundamental arrangement of magnets and windings. Once this has been selected, usually so as to create a desired wave mode, other aspects of the design, such as size, thickness of wear plate, mass, rigidity, heat tolerance and power handling, can be decided. These are practical choices that are constrained by the operating environment, and often limit the acoustic performance of the transducer as measured by, for example, the acoustic output amplitude or the prominence of the barkhausen noise. The design problem is therefore strongly affected by the fundamental method of the EMAT operation, which in some environments may preclude any practical solution.

SUMMARY OF THE INVENTION

It would be desirable to be able to provide an EMAT the construction of which is such as to provide significantly more flexibility in the design of the transducer, and which allows the transducer to be used in a wider range of operating environments than heretofore.

According to one aspect of the present invention there is provided an electromagnetic acoustic transducer for exciting ultrasound in a ferromagnetic material under test, the transducer comprising magnetic means arranged to be moved relative to the material under test to magnetise a surface layer of the material, and an electrical winding supplied by an alternating current source, the winding being arranged to be positioned adjacent the material subsequent to magnetisation thereof by the magnetic means, whereby the alternating magnetic flux created by the winding interacts with the remanent magnetisation of the material to create ultrasonic vibration of the material.

It will be appreciated that, with such an arrangement, the magnetic component of the transducer is physically separate from the electrical winding component, the two components of the transducer being applied in sequence to the material under test with an arbitrary time interval between the application of the two components.

Such separation of the two components has a very large effect on the possibilities of transducer design. In some specific applications, for example pipe inspection, a variety of technical and commercial advantages are achieved. Furthermore, barkhausen noise is eliminated.

The magnetic means, which may contain permanent magnet materials or an electromagnetic yoke, may be drawn linearly over the surface of the material under test or may be rolled over the surface. In each case the pattern of remanent magnetisation takes the form of one or more strips of differently orientated remanent magnetisation each following the trajectory of the magnetic means.

The continuous electrical winding may comprise one or more interconnected coils, which may be wound in a plane, for example as a pancake or meander coil, or wound around a ferromagnetic core, such as a C-core. In a preferred embodiment of the invention, the magnetic means and the electrical winding are linked together to be movable as a single assembly (albeit with some degree of flexibility to allow each to conform to the test surface), the electrical winding following the path of the magnetic means with a predetermined separation therebetween.

According to a further aspect of the present invention there is provided a method of exciting ultrasound in a ferromagnetic test material comprising the steps of establishing a pattern of remanent magnetisation in a surface layer of the material, and, subsequent to said magnetisation, applying alternating magnetic flux to the material to interact with the remanent magnetic field thereby to create ultrasonic vibration of the material.

BRIEF DESCRIPTION OF THE DRAWINGS

FIG. 3 shows, partly cut-away, an EMAT according to yet another embodiment of the invention.

DESCRIPTION OF THE PREFERRED EMBODIMENT

Figure 1:
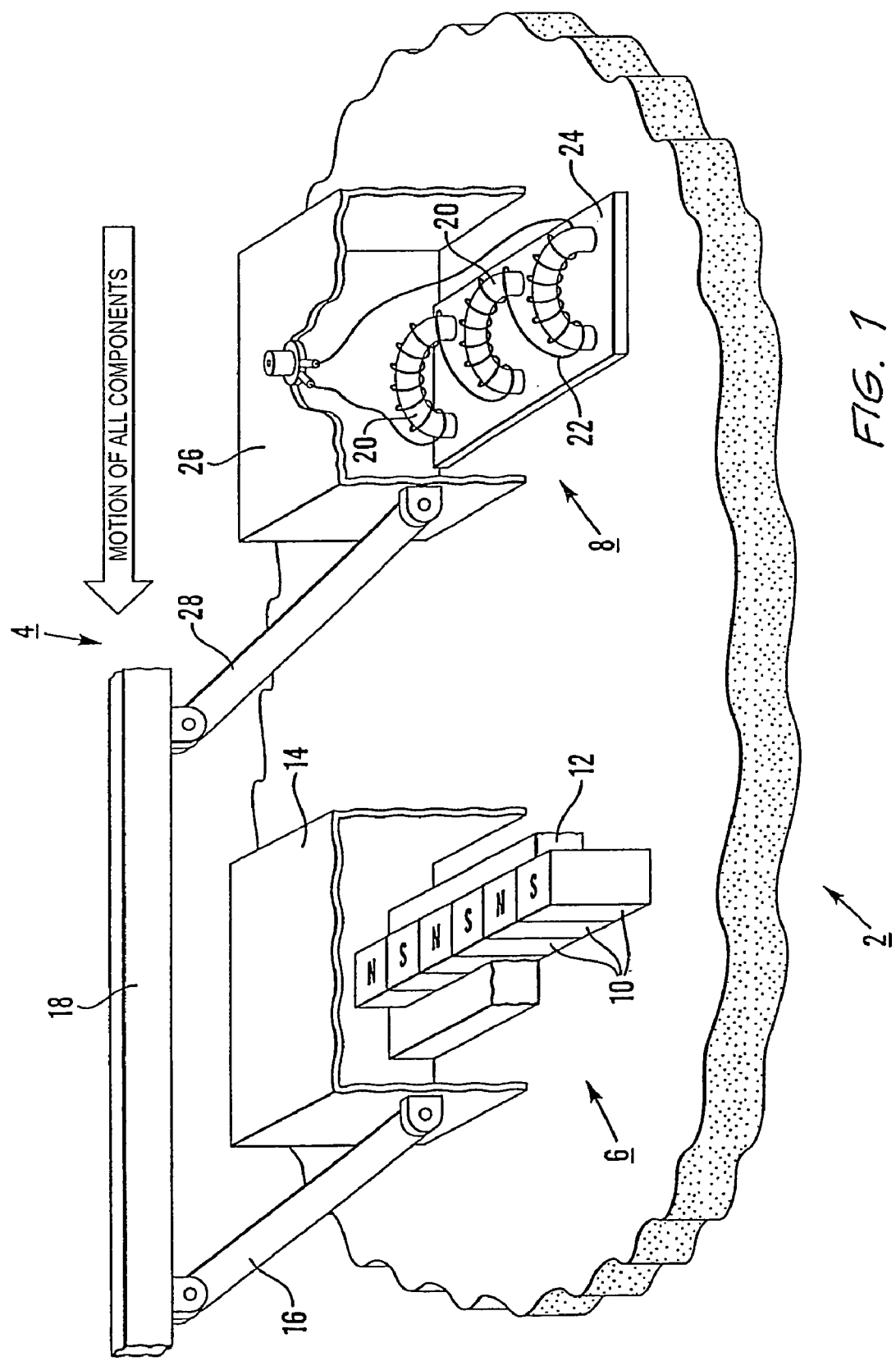
FIG. 1 shows, partly cut-away, an EMAT according to one embodiment the invention.

Referring to FIG. 1, a ferromagnetic material under test, which may be, for example, a high pressure steel gas pipeline, is indicated generally at 2, and an EMAT according to the invention is indicated generally at 4 for generating horizontally polarised guided shear waves.

The EMAT comprises two distinct and separate components, namely a magnetiser indicated generally at 6 and an electrical winding assembly indicated generally at 8.

The magnetiser 6 includes a linear array of magnets 10 with alternating magnetic poles N,S the centres of which are spaced apart by a distance equal to or shorter than half the wavelength of the desired ultrasound to be established in the material of the pipeline 2. The magnets 10 are shrouded by a band of wear resistant non-magnetic material shown partly cut away at 12 which does not interfere with or cover the underside of the magnets 10 but serves to limit the abrasion of the magnets 10 against the test material 2—the underside of the magnets 10 may make contact with the pipeline 2 or may be spaced therefrom by a very small gap.

The magnetiser 6 includes a housing 14 containing the magnets 10 and which allows convenient attachment of the magnetiser 6 by a first linkage 16 to a supporting structure 18 whereby the magnetiser 6 can be pulled along the test surface in a direction perpendicular to that of the array of magnets 10.

The electrical winding assembly 8 comprises a set of C-cores 20 the coils of which are interconnected with one another to form a single continuous winding 22. The cores 20 are mounted on a wear plate 24 of electrically insulating material adapted to engage the surface of the pipeline 2. The plate 24, which may be several millimetres thick whilst having negligible effect on the acoustic efficiency of the device when operating at frequencies useful for pipe inspection, protects the cores 20 from the material surface.

The assembly 8 includes a housing 26 which screens the cores 20 against electromagnetic interference, which is important when receiving acoustic signals, and which enables the assembly 8 to be readily connected to the supporting structure 18 by means of a second linkage 28. The assembly 8 is thus positioned rearwards of the magnetiser 6 with the cores 20 in a row perpendicular to the anticipated direction of travel and parallel to the row of magnets 10, the coils being positioned so that the magnetic flux produced by high frequency excitation of the cores 20 interacts with the surface of the test material 2.

In use, the magnetiser 6 and electrical winding assembly 8 are moved together by way of the linkages 16, 28 and the supporting structure 18 along the surface of the pipeline 2 such that the cores 20 follow the magnets 10 and with the winding 22 driven by a high frequency electrical source.

The magnets 10 magnetise the surface of the pipeline 2 as detailed above to establish remanent magnetisation therein, the subsequently applied high frequency alternating magnetic flux created by the assembly 8 interacting with this remanent magnetisation to initiate horizontally polarised shear waves within the pipeline 2 from the vicinity of the cores 20, the resultant ultrasound propagating substantially parallel with the row of cores 20.

If the assembly 8 is used as a receiver, the winding is sensitive to horizontal shear waves arriving from a direction substantially parallel with the row of cores 20.

Thus the EMAT of the invention effectively comprises two distinct components which may or may not be linked together mechanically. The first component is a magnetiser containing permanent magnet materials or an electromagnetic yoke which, when placed on or near the surface of a ferromagnetic test material and subsequently moved away, introduces a predefined pattern of remanent magnetism in a surface layer of the test material. The remanent pattern can be generated simply by dragging the device across the surface in a linear motion. In this case the remanent pattern takes the form of one or more linear strips of differently oriented remanent magnetisation, each strip following the trajectory of the magnetiser.

Figure 2:
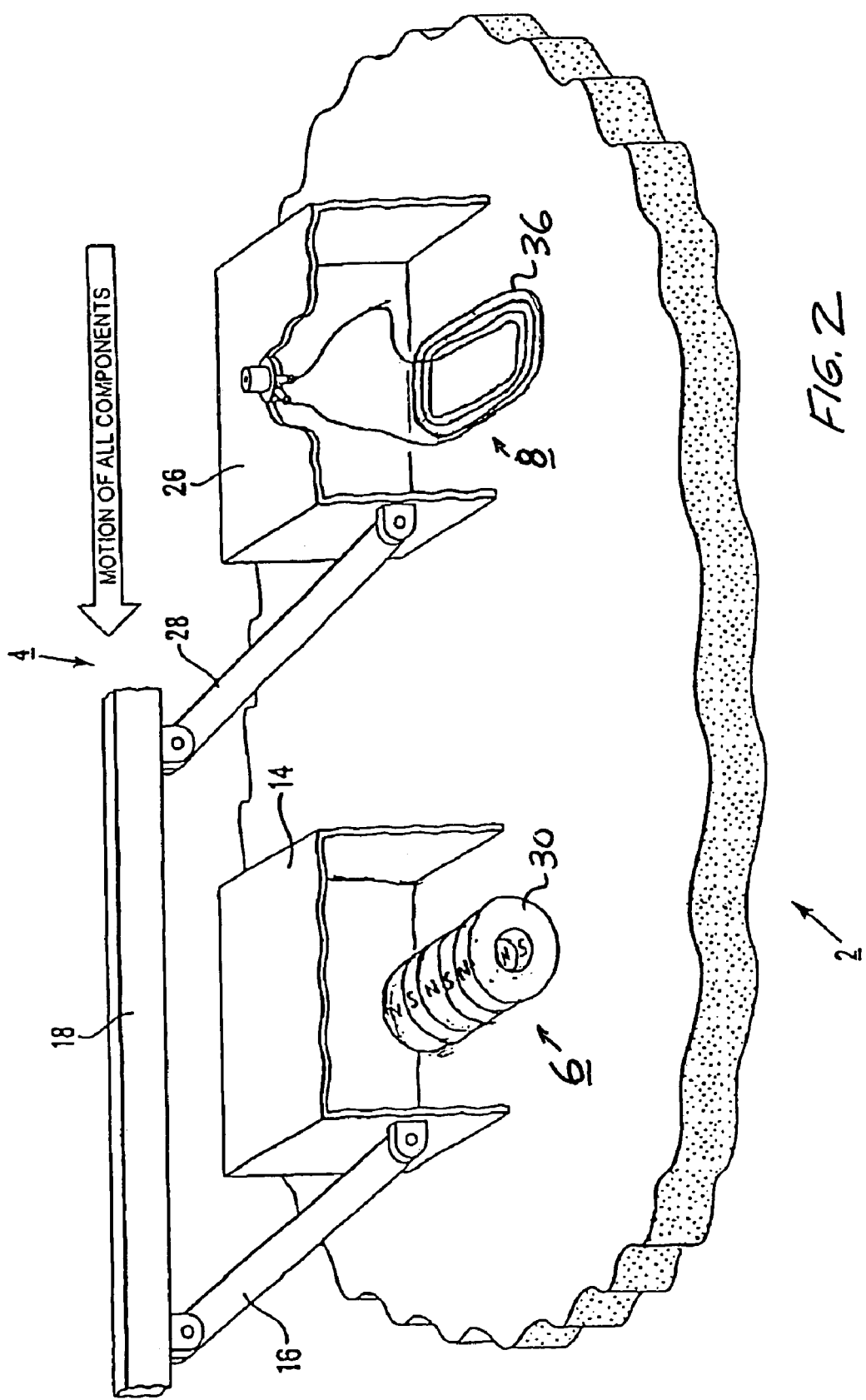
FIG. 2 shows, partly cut-away, an EMAT according to another embodiment of the invention.

In an alternative embodiment shown in FIG. 2, the magnetizer 6 may comprise a cylinder 30 incorporating a magnetic pattern and which can be rolled along the test material to create the remanent magnetisation which again may be in the form of one or more linear strips of differently orientated remanent magnetisation, each strip following the line of an associated magnetic portion of the cylinder. Alternatively, as illustrated in FIG. 3, the magnetiser 6 may be electromagnetic yoke 34, as described above.

The second component is an electrical winding assembly which, when placed close to the test material, is capable of generating a high frequency alternating magnetic flux in the surface of the material. A wide range of windings is possible, and some of these can be combined with high frequency electrical yokes. The winding arrangements can be those conventional to EMAT transducers with the exception that they have no fixed magnet arrangement associated with them. The winding component is arranged so that, when the high frequency alternating magnetic flux interacts with the pattern of remanent magnetisation, ultrasonic vibrations arise within the test material and propagate through it so as to allow ultrasonic inspection of the material. As an alternative to the illustrated C-cores shown in FIG. 1, the electrical winding assembly 8 may comprise one or more interconnected flat coils 36 of 'pancake' construction, as shown in FIG. 2 (and in FIG. 3).

The generation of ultrasound in the ferromagnetic test material is fundamentally achieved by a two-stage process. The first is the pre-conditioning of the ferromagnetic material, analogous to recording a magnetic pattern onto magnetic media such as magnetic tape. For any material having a significant remanence, such as structural steels, this pattern remains as a stable magnetic configuration in the test material after the passing or removal of the magnetiser. The second step is the introduction of the high frequency alternating magnetic flux, which interacts with the remanent magnetic pattern and initiates the ultrasound. If the ultrasound is to be received, the material is magnetically pre-conditioned as before, but the electrical winding is operated as a reception coil and converts the ultrasound into an electrical signal.

The described and illustrated arrangement shows the winding following in the path of the magnetising component, with a convenient separation between then, each dragged in linear fashion by a framework that supports both. This arrangement is particularly useful on pipeline inspection vehicles, and is suitable for both transmission and reception of ultrasound.

An important advantage of this type of EMAT is that, when operating as a receiver, that is with the winding acting as a listening device only, the EMAT is free from barkhausen noise. This is because the remanent magnetic pattern within the ferromagnetic material is stable, that is not evolving with time, within the frame of reference of the test material at the location of the receiver. This is true irrespective of whether the receiver is moving or not. This is different from a conventional receiver which would initiate barkhausen noise during its motion over the surface of the test material because the magnets contained in the receiver continuously modify the magnetisation state of the material.

Another important advantage of this type of EMAT is that the practical engineering of the two key components can be achieved independently. It is no longer necessary to accommodate the magnets around the windings or vice versa, since they no longer occupy the same physical region. Both components can have less mass than the conventional combined arrangement of windings and magnets, which improve the dynamics of the system. The magnetic clamping forces between the transducer and the test material are confined to the magnetiser, and hence the wear problems occur principally on only one unit. The wear problem can then be solved by unconventional means, for example by allowing significant wear to occur and using disposable yoke faces rather than hardened wear surfaces. In addition, the thickness of the wear plate or shoe used with the electrical winding can be much greater than normally used by an EMAT. This is because the winding is highly tolerant to 'lift-off', since theremanent field is impressed into the test material and does not diminish with lift-off. This contrasts with a normal EMAT, where the source of field lifts from the surface along with the winding, and the efficiency reduces very rapidly with lift-off.

The EMAT of the invention compares extremely favourably with existing EMATS for generating horizontally polarised shear waves which use an array of magnets in close proximity to each other. In such known cases, the applied field at the surface of the plate changes rapidly in amplitude and direction for small changes in spatial position within the plate material immediately underneath the transducer. The complexity of the field pattern makes these transducers particularly susceptible to motion-induced barkhausen noise. Additionally, existing EMATs for operating in pipeline environments are bulky, suffer from acute loss of efficiency with sensor lift-off, and are severely effected by abrasion.

What is claimed is:

1. An electromagnetic acoustic transducer for exciting ultrasound in a ferromagnetic material under test, the transducer comprising magnetic means comprising a linear array of magnets with alternating magnetic poles, arranged to be moved relative to the material under test to magnetize a surface layer of the material, and an electrical winding supplied by an alternating current source; characterized in that:
the centers of said alternating magnetic poles are spaced apart by a distance equal to or shorter than half the wavelength of said ultrasound, and the electrical winding is spaced from the array of magnets so that the magnetic means and the electric winding are arranged to be applied in sequence to the material under test whereby the electrical winding is for positioning adjacent the material subsequent to magnetization thereof by the magnetic means, the alternating magnetic flux created by the winding being arranged to interact with the remanent magnetization of the material to create ultrasonic vibration of the material.

2. A transducer as claimed in claim 1 in which the magnetic means contains permanent magnet materials or an electromagnetic yoke.

3. A transducer as claimed in claim 1 in which the electrical winding comprises a continuous electrical winding composed of one or more interconnected coils.

4. A transducer as claimed in claim 3 in which the coils are wound in a plane, or wound around a ferromagnetic core.

5. A transducer as claimed in claim 1 in which the magnetic means and the electrical winding are linked together to be movable as a single assembly, the electrical winding following the path of the magnetic means with a predetermined separation therebetween.

6. A method of exciting ultrasound in a ferromagnetic test material comprising:
pre-conditioning a surface layer of the ferromagnetic material, said pre-conditioning comprising applying a magnetic field thereto using a magnetizer, and removing said magnetizer or causing said magnetizer to pass from said surface layer, thereby establishing a pattern of remanent magnetization in the surface layer of the material; and
subsequently applying alternating magnetic flux to the material to interact with the remanent magnetic field thereby to create ultrasonic vibration of the material.

7. A method as claimed in claim 6 using an electromagnetic acoustic transducer as which comprises magnetic means comprising a linear array of magnets with alternating magnetic poles, arranged to be moved relative to the material under test to magnetized a surface layer of the material, and an electrical winding supplied by an alternating current source;
characterized in that: the centers of said alternating magnetic poles are spaced apart by a distance equal to or shorter than half the wavelength of said ultrasound, and the electrical winding is spaced from the array of magnets so that the magnetic means and the electric winding are arranged to be applied in sequence to the material under test whereby the electrical winding is for positioning adjacent the material subsequent to magnetization thereof by the magnetic means, the alternating magnetic flux created by the winding being arranged to interact with the remanent magnetization of the- material to create ultrasonic vibration of the material.

8. A method as claimed in claim 7 in which the magnetic means is drawn linearly over the surface of the material under test.

9. A method as claimed in claim 7 in which the magnetic means is rolled over the surface of the material under test.

* * * * *